(12) United States Patent
Dragan

(10) Patent No.: US 6,379,152 B1
(45) Date of Patent: Apr. 30, 2002

(54) DENTAL CAPSULE FOR PLACEMENT OF ULTRA-HIGH VISCOSITY DENTAL COMPOSITE MATERIAL

(75) Inventor: William B. Dragan, Easton, CT (US)

(73) Assignee: Centrix, Inc., Shelton, CT (US)

( * ) Notice: Subject to any disclaimer, the term of this patent is extended or adjusted under 35 U.S.C. 154(b) by 0 days.

(21) Appl. No.: 09/605,495

(22) Filed: Jun. 28, 2000

Related U.S. Application Data

(63) Continuation-in-part of application No. 09/552,338, filed on Apr. 19, 2000, now Pat. No. 6,261,094.

(51) Int. Cl.⁷ .................................................. A61C 5/04
(52) U.S. Cl. ....................................................... 433/90
(58) Field of Search .................... 433/89, 90; 222/386; 401/176

(56) References Cited

U.S. PATENT DOCUMENTS

| | | | |
|---|---|---|---|
| 2,903,794 A | * | 9/1959 | Carfagni ..................... 433/90 |
| 3,581,399 A | | 6/1971 | Dragan |
| 4,330,280 A | | 5/1982 | Dougherty et al. |
| 4,384,853 A | | 5/1983 | Welsh |
| 4,391,590 A | | 7/1983 | Dougherty |
| 4,767,326 A | | 8/1988 | Bennett et al. |
| 4,801,263 A | * | 1/1989 | Clark .......................... 433/90 |
| 4,963,093 A | | 10/1990 | Dragan |
| 4,969,816 A | | 11/1990 | Drumm |
| 5,083,921 A | | 1/1992 | Dragan |
| 5,100,320 A | | 3/1992 | Martin et al. |
| 5,129,825 A | | 7/1992 | Discko, Jr. |
| 5,165,890 A | | 11/1992 | Discko, Jr. |
| 5,172,807 A | | 12/1992 | Dragan et al. |
| 5,322,440 A | | 6/1994 | Steele |
| 5,460,523 A | | 10/1995 | Schulman |
| 5,591,027 A | * | 1/1997 | Muhlbauer ................... 433/90 |
| 5,707,234 A | | 1/1998 | Bender |
| 5,722,830 A | * | 3/1998 | Brandhorst et al. ........... 433/90 |
| 5,893,714 A | * | 4/1999 | Arnold et al. ................. 433/90 |
| 5,938,439 A | * | 8/1999 | Mertins et al. ................ 433/90 |
| 6,102,699 A | * | 8/2000 | Galehr et al. ................. 433/90 |

* cited by examiner

Primary Examiner—Todd E. Manahan
(74) Attorney, Agent, or Firm—Fattibene & Fattibene; Paul A. Fattibene; Arthur T. Fattibene

(57) ABSTRACT

This disclosure is directed to a capsule construction for dispensing the entire volume of dental composite material contained therein, wherein the capsule includes a body portion defining a reservoir for containing a predetermined amount of dental material and having an opening at one end and a connected angularly disposed discharge nozzle with a passageway extending therethrough terminating at a discharge orifice at the other end of the body portion. A displaceable piston in the form of an elongated rod or cylinder seals the open end of the capsule body portion. The piston is formed of a flexible material which is sufficiently rigid to extrude the material within the reservoir when displaced, e.g. by a syringe device, yet sufficiently flexible to negotiate the angular turn at the nozzle end so as to extend through the passageway of the discharge nozzle to effect the extrusion of all of the material contained within the reservoir.

7 Claims, 3 Drawing Sheets

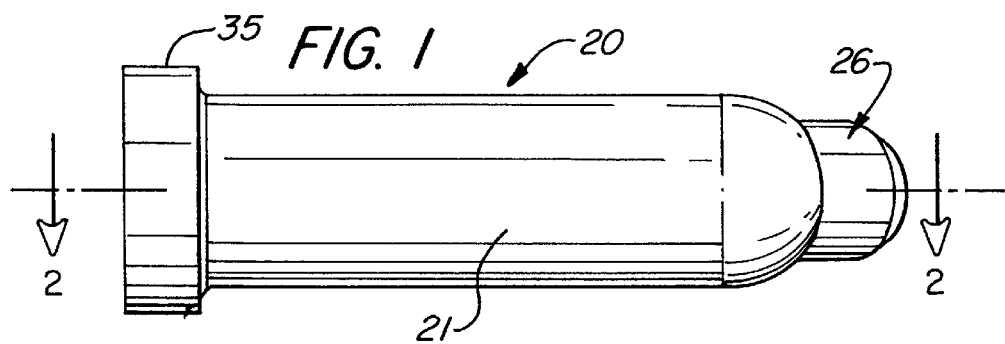
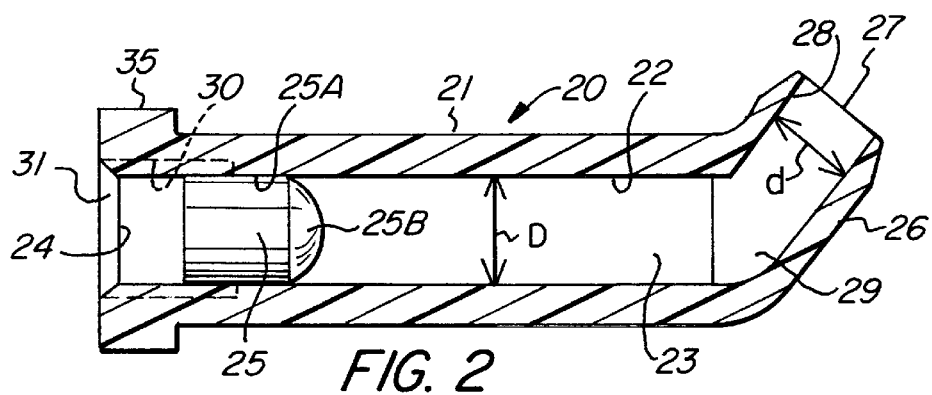
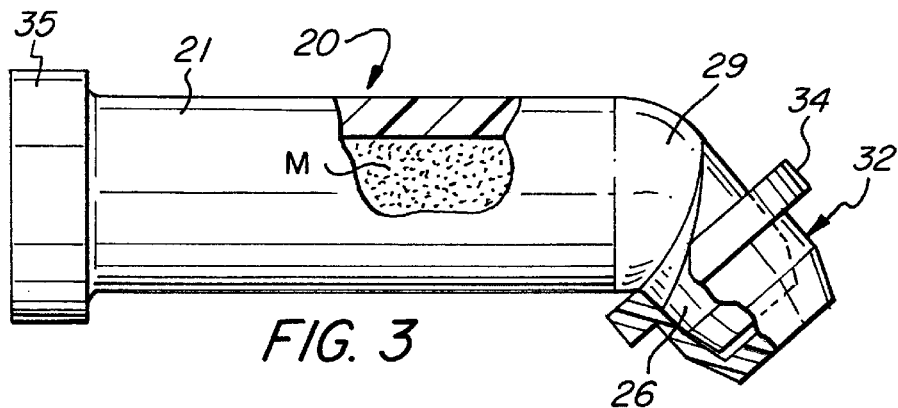
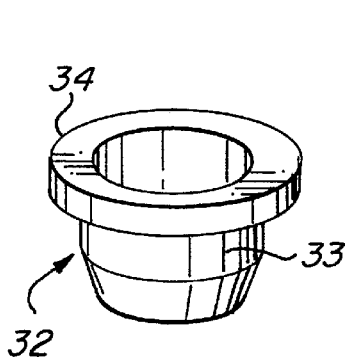
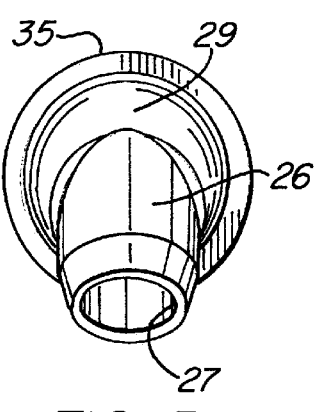
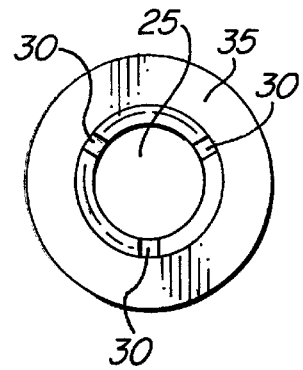

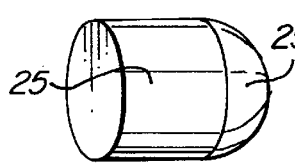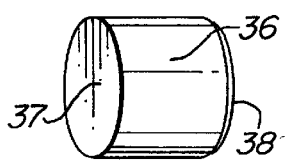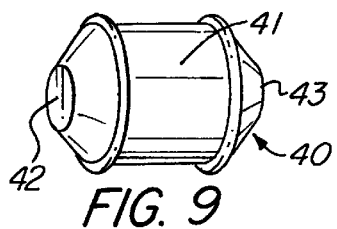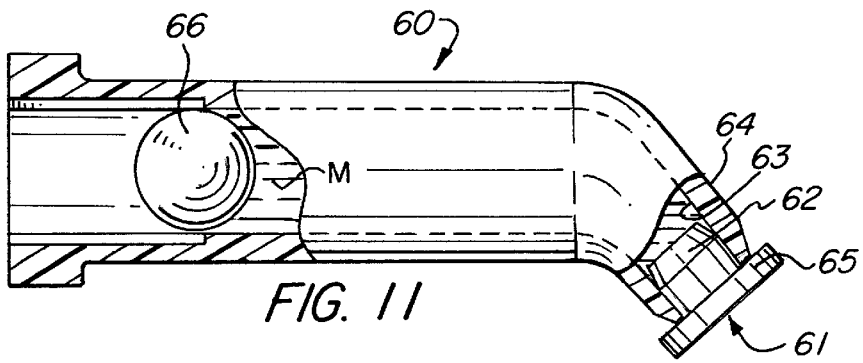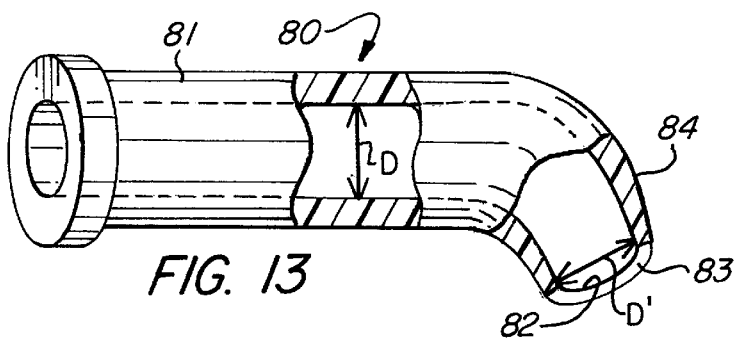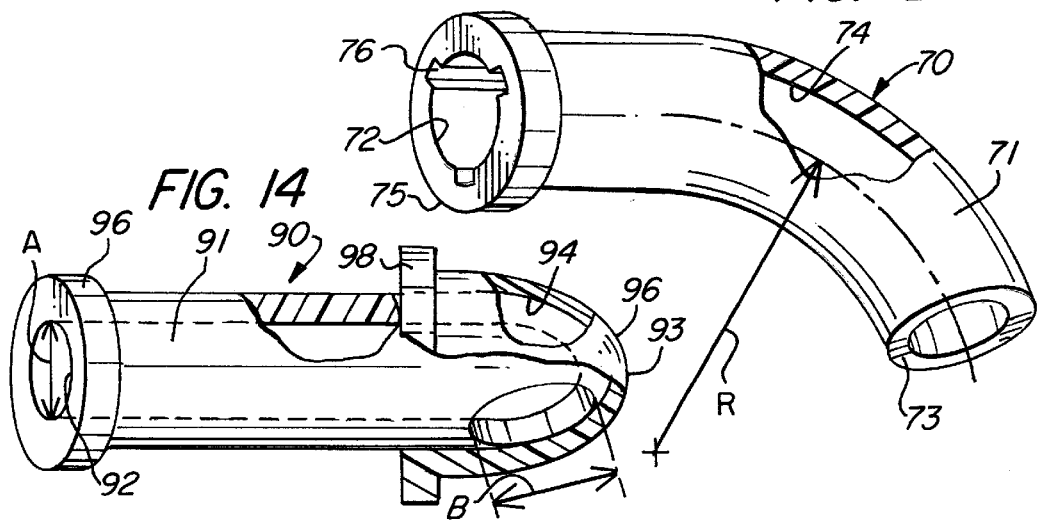

DENTAL CAPSULE FOR PLACEMENT OF ULTRA-HIGH VISCOSITY DENTAL COMPOSITE MATERIAL

RELATED APPLICATION

This is a continuation-in-part application of application Ser. No. 09/552,338 filed Apr. 19, 2000, now U.S. Pat. No. 6,261,094 granted Jul. 17, 2001.

FIELD OF THE INVENTION

This invention is directed generally to a dental capsule for the direct placement of composite type restorative dental material, and more specifically to a unit dose dental capsule for the direct placement of ultra-high density, i.e. packable or condensable composite or heavy viscosity materials to a prepared tooth by syringing.

BACKGROUND OF THE INVENTION

Dental composite material for restoring teeth was first introduced into dentistry about the mid 1960's. The initial composites had a paste-like consistency. As a result, dentists encountered considerable difficulty in the placement of such composite material into a prepared tooth. Generally, the dentist would apply such paste-like composite resin material to a tooth by means of a spatula, palate or like tool. This manual technique resulted in the tooth being filled from the outside in. It was noted that this spatula technique of placing such composite resulted in the formation of voids within the finished restoration. This was because the spatula or palate technique of placing such material in a tooth could not satisfactorily pack the paste composite material into the small and difficult to reach areas of the tooth. The placement of such composite material with a palate or spatula also resulted in the entrainment of air and the formation of air bubbles in the composite material as it is being placed. The formation of such voids or air bubbles compromised the strength and durability of the finished restoration. A further difficulty that was encountered by the dentist was that such composite material had a tendency to stick to the palate or spatula, causing the material to be pulled away when the dentist removed the palate or spatula. Also, if a dentist used a metal instrument to place the composite material, there was a tendency of the metallic instrument to react and discolor the composite.

The problems initially encountered by the dentist in placing such composite resins were solved by the development of the syringing technique for the placement of such composite materials. This syringing technique was first disclosed in U.S. Pat. No. 3,581,399 granted Jun. 1, 1971 to Dr. William B. Dragan. The syringing technique and unit dose capsules disclosed in said U.S. Pat. No. 3,581,399 was followed up by other capsule improvements as disclosed in U.S. Pat. Nos. 4,963,093; 4,969,816; 5,083,921; 5,129,825; 5,165,890 and 5,172,807. These known capsule constructions proved satisfactory for placing the composite materials having a paste-like consistency and/or a composite material having a filler content of less than 78% by weight.

Other known capsules from which such paste-like composites could be syringed are disclosed in U.S. Pat. Nos. 4,330,280; 4,384,853; 4,391,590; 4,767,326; 5,100,320; 5,322,440; 5,460,523 and 5,707,234.

Generally, these known capsules are provided with a reservoir portion for containing a predetermined supply of dental material having an internal diameter which is substantially greater than the internal diameter of the discharge orifice. These known capsule constructions have been designed to handle and be used with the then available composites having a paste-like consistency, i.e., a composite resin composition having a filler content of 78% by weight or less. The lower the filler content, the less viscous the material, and the more readily it can be syringed through the relatively small discharge orifice of the known capsule designs.

It has also been observed in the prior known capsule constructions that the arrangement was such that it was never possible to attain total evacuation of the dental material from the capsule so matter how flowable the material. This was because a portion of the material always remained in the nozzle portion of the capsule as the displacement of the plug or piston was limited by the end wall of the capsule. As a result, the portion of the dental material remaining in the nozzle of the capsule was always wasted.

More recently, the composite dental materials are being formulated with a substantially larger filler content, i.e., more than 78% filled whereby such highly filled or ultra dense composites are rendered "packable" or "condensable" to imitate amalgam in consistency. Such ultra dense or condensable composite materials are particularly suitable for restoring the back or posterior teeth. The particular condensable properties of such ultra dense composite materials makes it difficult to dispense from bulk syringes. The extreme viscous properties of such ultra dense dental composites have also prohibited the placement of such ultra dense composite material by the use of the syringing technique utilizing the known capsule constructions, which the dental profession has virtually universally adopted as the preferred method of delivering a composite material directly into a prepared cavity.

SUMMARY OF THE INVENTION

An object of this invention is to provide a capsule construction particularly suitable for effecting the placement of ultra dense or highly filled composite resin dental restorative materials by means of the syringing technique.

Another object is to provide a capsule construction for dispensing an ultra dense or packable composite resin material directly to a tooth in a manner to minimize any formation of voids.

Another object is to provide a capsule and plug arrangement which is particularly suitable for packaging and dispensing an ultra dense compactable composite resin material.

Another object is to provide a capsule and plug arrangement constructed so as to insure that the entire amount of material contained in the capsule is completely discharged or ejected from the capsules so as to completely eliminate any waste.

The foregoing objects and other features and advantages are attained by a capsule construction having a generally cylindrical shaped body portion defining a reservoir for receiving a predetermined amount of ultra dense dental composite resin material. The body portion is provided with a full opening at one end with the other end thereof terminating in a nozzle having a discharge orifice disposed at an angle relative to the central longitudinal axis of the body portion. The body portion defining the reservoir is provided with an internal diameter which is equal to or only slightly larger than the internal diameter of the nozzle or discharge orifice. The internal surface or bore of the body portion is uniform and smooth throughout and is connected in communication with the passageway of the nozzle so as to be free of any obstruction to provide for a smooth transition therebetween. The ratio between the internal diameter of the nozzle discharge orifice or opening (d) relative to the internal diameter of the body portion (D) preferably ranges between 1 to 1 to 0.60 to 1. The open end of the body portion is sealed by a displaceable piston or plug which may be spherical, cylindrical or rod-like and/or a combination thereof so as to be rendered bi-directional. Adjacent the open end, the internal surface of the body portion is provided with one or more longitudinally extending venting grooves to facilitate the venting of any entrapped air upon the insertion of the displaceable piston. A laterally extending collar or flange circumscribes the open end of the body portion and a sealing member is fitted to the nozzle for sealing the discharge orifice. In one form of the invention, the displaceable piston comprises a flexible elongated rod which is generally uniform in cross-section so as to be snugly received in the open end of the capsule to seal the material therein which, when displaced, can readily flex about the transition area and slide through the bore of the nozzle to eject all the material from the bore of the nozzle.

IN THE DRAWINGS

FIG. 1 is a top plan view of a dental capsule embodying the invention.

FIG. 2 is a sectional view taken on line 2—2 of FIG. 1.

FIG. 3 is a side view of the capsule of FIG. 1 with a sealing cap and having portions broken away.

FIG. 4 is a detail perspective view of the sealing cap.

FIG. 5 is a front end view of the capsule of FIG. 1 with the sealing cap removed.

FIG. 6 is a rear or left end view of FIG. 2.

FIG. 7 is a perspective view of a piston for use with the capsule of FIG. 1.

FIG. 8 is a perspective view of a modified piston construction.

FIG. 9 is a perspective view of another modified piston construction.

FIG. 10 is a perspective view of another modified piston construction.

FIG. 11 is a modified form of the invention.

FIG. 12 is a perspective view of another modified embodiment.

FIG. 13 is a perspective view of still another embodiment.

FIG. 14 is a perspective view of still another embodiment.

DETAIL DESCRIPTION

Figure 15:
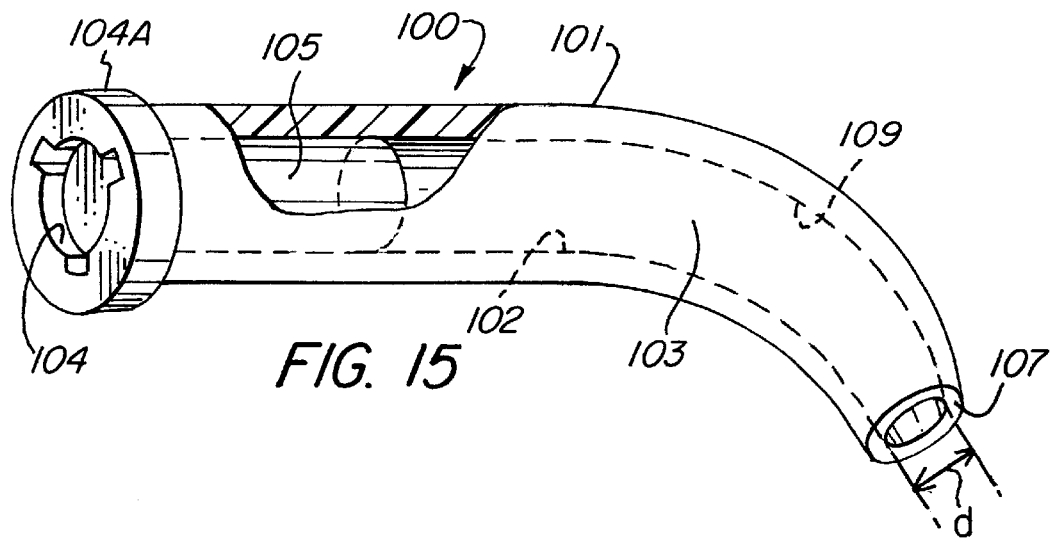
FIG. 15 is a perspective view of a modified form of the invention having parts broken away.

Referring to the drawings, there is illustrated in FIGS. 1 to 3 one form of the invention. As shown, the dental capsule 20 is specially constructed for use with ultra high density dental composite restorative material. Ultra high density dental composite material as used herein is defined as a dental composite restorative resin material having in excess of 78% by weight of a filler material which may comprise barium, aluminum silicate, fumed silica, glass, quartz or other inorganic fillers commonly used by the makers of composite resin dental material. Composite resin material having a filler content in excess of 78% renders the composition "condensable" or "packable" to simulate amalgam, which renders such ultra highly dense composites suitable for restoring the molars or back teeth. Heretofore, such ultra dense composites could not be placed by utilizing the preferred syringing technique, which is now widely accepted as the preferred method of placing composites in effecting a tooth restoration.

In order to render such ultra dense composites syringeable so as to attain all of the benefits attributed to the syringing technique, the capsule construction 20 is provided with a cylindrical body portion 21 having an internal bore 22 defining a reservoir 23 for containing a predetermined amount of ultra dense composite material M. One end of the capsule body portion 21 is provided with a full open end 24 which is sealed or closed by a displaceable piston 25, as will be herein described. It will be noted that the bore 22 is of a generally uniform diameter throughout the length of the body portion 21.

Connected to the other end of the body portion 21 is an angularly disposed nozzle 26 terminating in a discharge orifice 27. The passageway 28 formed in the nozzle and terminating at the discharge orifice 27 also has a generally constant diameter throughout the length thereof. At the bend defined by the intersection of the axis of the nozzle passageway 28 and the axis of the body portion, there is formed a slight transition zone 29. The arrangement is such that the internal walls defining the nozzle passageway 28, the bore 22 of the capsule body 21, and the transition zone 29 therebetween are free of any obstruction so as to permit the uninterrupted flow of the ultra dense material therethrough with a minimum of any resistive forces acting thereon during the extrusion of the ultra dense material M. To achieve this result, the optimal ratio of the internal diameter "D" of the bore 22 relative to that of the internal diameter "d" of the passageway 28 is 1 to 1 or approximately 1 to 1. However, it will be understood that this ratio may vary slightly. For example, if the diameter "D" of bore 22 is 0.150 inches and diameter "d" of the nozzle passageway 28 is equal to 0.125 inches, satisfactory results can still be obtained. Thus, the ratio of relative diameters, i.e. d/D of this example is 0.83, which is slightly less than the optimal ratio of 1 to 1. The lower ratio permits a slight reduction of the internal diameter of the nozzle discharge passageway 28 relative to that of the internal bore 22 to accommodate the placement of the material into a smaller prepared cavity of the tooth to be restored by the syringing technique. An optimum ratio of said diameters d/D may range between 0.60 to 1.

It will be understood that the ultra dense material M placed in capsule 20 can be readily extruded by placing the capsule in any of the known syringe guns, e.g. such as disclosed in U.S. Pat. No. 4,198,756 and those subsequently patented which embody the mechanical advantage of U.S. Pat. No. 4,198,756.

As best seen in FIG. 2, one or more venting grooves 30 may be formed in the internal wall of the body portion 21 adjacent the open end 24. As shown, the venting grooves 30 define a vent means through which any air entrapped within the capsule may be displaced when the piston 25 is inserted to seal the material M therein. With the piston 25 in place, the piston effectively seals off the vent grooves 30 to the outside atmosphere.

Piston 25 is provided with a cylindrical portion 25A having a diameter sized so as to be frictionally received within the bore 22 of the capsule body. The leading end 25B of the piston is curvilinear to complement the slight curvature of the transition zone 29 so that a maximum amount of the material within the reservoir 23 may be extruded.

In the illustrated embodiment, the mouth 31 of opening 24 diverges slightly outwardly, as indicated, to facilitate the insertion of piston 25. It will thus be apparent that as the piston 25 is displaced by the force of the syringe plunger acting on the piston as disclosed in U.S. Pat. No. 4,198,756, the dense material M is expressed as a "rod" through the discharge orifice 27, with a minimum of resistance, other than sliding resistance.

To seal the discharge orifice to prevent any contamination of the material within the capsule and/or to prevent any light from penetrating, in the event the material M is light activated, a sealing cap 32 is provided. In the illustrated embodiment, the sealing cap 32 is provided with a cup shaped body 33 sized to be frictionally retained on the discharge nozzle 26. Circumscribing the opening of the sealing cap 32 is a laterally extending circumscribing flange 34.

It will be understood that in the event the dental material is light activated, the capsule is fabricated of a material that is opaque to the actinic light of the dental material as more particularly set forth in U.S. Pat. No. 5,122,057, which is incorporated herein by reference.

The capsule 20 may also be provided with a laterally extending flange or collar 35 which circumscribes the open end 24.

To minimize any resistance attributed to sliding friction between the ultra dense material M and the internal walls of the capsule, when a force is being applied to the piston 25 to extrude the material out of the capsule, the internal walls or surfaces of the capsule may be lightly coated or lubricated with a material that does not interfere with the chemistry of the composite material. Preferably, the coating material should comprise a component of the composite composition itself. As the composite material includes as a part thereof a liquid monomer, said liquid monomer may be used to lubricate the internal surfaces of the capsule without adversely effecting the chemistry of the composition. Coating the internal walls of the capsule with the liquid monomer results in (1) minimizing frictional resistance between the material M and the internal walls of the capsule due to sliding friction and (2) minimize any loss of the liquid portion of the composite material as it is being extruded due to the pressure or force being imparted to the material as it is being extruded. It will be understood that the lubricant may also comprise a silicone or Teflon, which may be applied to the inner surfaces of the capsule or be added to the material out of which the capsules may be molded, in which case the lubricating material is integrally molded in the capsule.

FIGS. 8, 9 and 10 illustrate other alternative piston construction which may be utilized in the capsule 20 described. The piston 36 of FIG. 8 comprises a cylindrical body having opposed flat or blunt ends 37, 38. The piston 36 has the advantage of ease of manufacture as the piston 36 can be readily fabricated by forming a rod and thereafter severing such rod into several parts to form the piston 36. Thus, a mold is not essential in forming a piston 36.

FIG. 9 illustrates another modified piston construction. Piston 40 of FIG. 9 includes a central cylindrical body portion 41 having similar or identical spheroidal end portions 42, 43. It will be understood that the opposed end portions 42, 43 may be hemispherical, ellipsoidal or other curvilinear or arcuate shape. The advantage of piston 40 is that it is immaterial which end of the piston 40 is first inserted into the open end of the capsule. Thus, the piston construction of FIGS. 8 and 9 are bidirectional which is important during the assembly and/or filling of the described capsule.

FIG. 10 illustrates a piston 50 which is formed in the shape of a sphere. It will be understood that the diameter of the sphere shaped piston 50 is such that the outer surface of the sphere piston 50 is disposed in sealing relationship to the internal walls of the capsule body, as seen in FIG. 11. The spherical piston 50 has the advantage that when used, it defines a line contact seal with the internal walls of the capsule and minimizes any sliding friction between the piston 50 and the internal walls of the capsule. Also, the piston 50 eliminates any need to orient the piston 50 relative to the capsule during assembly.

FIG. 11 illustrates a modified form of the invention. In this form, the capsule construction 60 is identical to that described with respect to FIGS. 1 to 3. However, in the embodiment of FIG. 11, the nozzle of the capsule 60 is sealed by an end plug 61. The end plug has a stem 62 sized to seal the passageway 63 formed in the nozzle 64 of capsule 60. Connected to the stem 62 is a flange 65 which functions as a stop to limit the insertion distance of the stem 62. With the plug 61 in place as shown in FIG. 11, the orifice opening of the nozzle is tightly sealed. The piston 66 shown in FIG. 11 comprises a spherical piston, hereinbefore described with respect to FIG. 10. In all other respects, the construction and functioning of capsule 60 is similar to that described with respect to capsule 20 of FIGS. 1 and 2.

FIG. 12 is a perspective view of a further modification of the invention. In this form, the capsule 70 has a curvilinear body 71 of a predetermined radius R to define a smooth uninterrupted passageway extending from the open end 72 of the capsule 70 to the discharge orifice 73. In this form of the invention, the passageway or bore 74 has a uniform diameter throughout the length of the body 71. It will be understood that the orifice 73 is sized so as to minimize any resistant forces during extrusion of the ultra dense composite material. In this form of the invention, the spherical piston 50 would be ideal for extruding the material through the nozzle orifice 73. A laterally extending flange or collar 75 circumscribes the opened end 72. Capsule 70 may also be provided with one or more venting grooves 76 of the type hereinbefore described with respect to the embodiment of FIG. 2.

It will be understood that the discharge orifice 73 of capsule 70 may be sealed either by a sealing cap 32 or end plug 61 as previously described with respect to FIGS. 3 and 10.

In this form of the invention, the bore of the capsule body 71 is of uniform or constant diameter D from the open end 72 to the discharge orifice 73 so as to have the optimum ratio of 1 to 1 as hereinbefore described.

In all other respects, the operation or functioning of capsule 70 is similar to that hereinbefore described.

FIG. 13 illustrates another slightly modified embodiment. As shown, the capsule 80 is virtually similar to that of FIGS. 1 to 3 with the exception that the internal diameter D of the capsule cylindrical body portion 81 is equal to diameter D' of the nozzle passageway 82, which terminates at the discharge orifice 83. The nozzle portion 84 is angularly disposed similar to that described with respect to FIGS. 1 to 3. In all other respects, the capsule 80 is similar in structure and function to that described with respect to FIGS. 1 to 3.

FIG. 14 illustrates yet another embodiment. In this embodiment, the capsule 90 has a body portion 91 which defines the reservoir for containing a predetermined amount of the ultra-high density or viscous material. Capsule 90 is provided with a bore having a uniform or constant diameter D therethrough and is open at one end 92. The other end 93 is closed by a sloping or curvilinear end wall 94. In this form of the invention, the discharge orifice 95 is disposed in the wall portion of the capsule body adjacent the end wall 94. Circumscribing the open end 92 is a lateral extending circumscribing flange 96. It will be understood that any of the pistons hereinbefore described may be used to seal the ultra high viscosity material within the capsule 90.

In this form of the invention, the discharge orifice 95 is formed with a diameter "d" which may be equal to or slightly less than diameter "D" of the bore of capsule 90 so as to define a ratio of $$\frac{\text{"}d\text{"}}{\text{"}D\text{"}}$$

ranging between 0.60 to 1.

To seal the discharge orifice 95, capsule 90 is provided with a sealing cap 97 which is frictionally fitted to the closed end 93 of the capsule 90 with sufficient depth to seal the orifice 95. The open end of the seal cap 97 is provided with an outwardly extending flange 98, which provides an edge to facilitate the placement of the sealing cap 97 onto and off the closed end 93 of the capsule 90. In all other respects, the construction and operation of capsule 90 is similar to that hereinbefore described.

FIG. 15 illustrates another modified embodiment of this invention. In this form, the capsule 100 comprises a body portion 101 having an internal bore 102 defining a reservoir 103 for receiving a predetermined amount of dental material as hereinbefore described. The internal diameter "D" is equal to or only slightly greater than the internal diameter "d" of the discharge orifice opening 107. In this form of the invention, the walls 107A defining the discharge nozzle 106 are made thinner than the thickness of the walls defining the body 101 or reservoir portion of the capsule 100. In other words, the outer surface of the nozzle may taper inwardly slightly in the direction of the discharge orifice 107. This slight thinning of the walls defining the nozzle 106 imparts a slight flexibility to the walls of the discharge end at the nozzle 106.

The end of the body portion 101 opposite the discharge nozzle 106 is fully opened as hereinbefore described for receiving the dental material, and which opening 104 is sealed by a displaceable piston 105.

In this form of the invention, the piston comprises an elongated rod formed of a suitable flexible material that is sufficiently rigid to effect the extrusion of the material when the piston 105 is displaced, yet flexible enough to negotiate the transition area 109 between the reservoir portion and the connected nozzle 106. As shown in FIG. 15, the outside diameter of the displaceable piston 105 forms a snug fit with the internal diameter "D" of the capsule body portion 101 to form a seal thereat, and yet is rendered freely slideable when displaced to extrude the dental material. In the event that the diameter "d" of bore or passageway 108 of the nozzle 106 is slightly less than the diameter "D" of the body portion 101 of capsule 100, the thinning of the nozzle walls 107A toward the discharge opening or orifice 108 renders the nozzle walls sufficiently flexible so as to permit the piston 105 to be pushed therethrough during the syringing operation so as to insure complete evacuation of the dental material. It will be noted that when the piston 105 is displaced to the position shown in FIG. 16, all of the material which had been placed within the reservoir or body portion 101 has been extruded therefrom, so that none remains within the bore or passageway 108 of the capsule.

Figure 16:
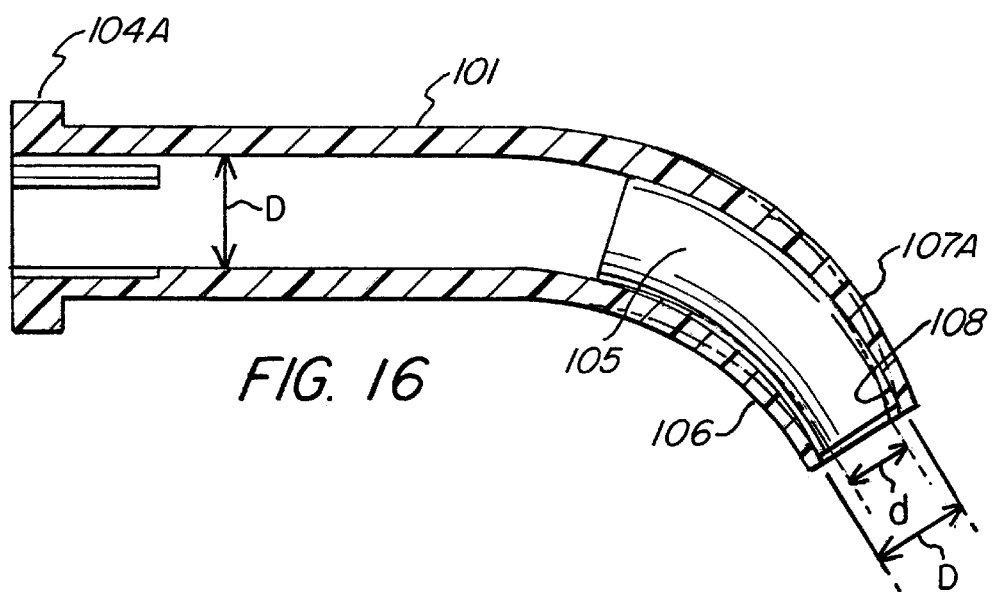
FIG. 16 is a sectional view of FIG. 15 illustrating the piston in the fully extruded position.

To accomplish total evacuation, it is preferred that the piston 105 be formed of a Teflon material as such material is self lubricating, and will freely slide while maintaining a positive seal with the internal surface of the reservoir, and is sufficiently flexible to negotiate the smooth transition area 109, as seen in FIG. 16.

It will be further understood that the rod shaped piston 105 is rendered bi-directional in that it is immaterial which end is inserted into the capsule body to seal the material therein. In the illustrated embodiment, the opposed ends 105A, 105B of the piston 105 are blunt or flat. However, the same bi-directional result may be achieved if the opposed ends 105A, 105B were made curvilinear, e.g. hemispherical or conical.

A circumscribing flange 104A circumscribes the open end 104 as previously described.

The piston 105 is sufficiently long so as to insure that all of the material within the bore or passageway of the nozzle is extruded. To achieve this end result, the piston is formed of a suitable material, e.g. Teflon, that is sufficiently flexible to negotiate the gentle curve in the transition zone 109, and sufficiently compressible for passage through the bore or passage of the nozzle in the event the internal diameter "d" of the orifice or discharge opening is less than "D" or equal to or greater than "d". Alternatively, the walls of the nozzle may be tapered as hereinbefore described so as to render the walls of the nozzle sufficiently flexible so as to permit the piston 105 to slide therethrough as noted in FIG. 15.

Figure 17:
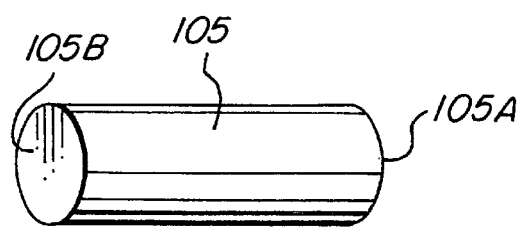
FIG. 17 is a detail side view of the piston of FIGS. 15 and 16.

In all other respects, the construction of the embodiment of FIGS. 15 to 17 is similar to that hereinbefore described, e.g. the capsule of FIGS. 15 and 16 may have its discharge nozzle sealed by an end cap as hereinbefore described and provided with vent means, also as described.

The capsule of FIGS. 15 and 16 is particularly suitable for dispensing and placing ultra-dense or compactable composite material. As such materials are relatively expensive, the elimination of any possible waste is an important aspect of this invention.

From the foregoing, it will be noted that the principle common to each of the described embodiments for rendering ultra dense, compactable or condensable material syringeable so as to prohibit the formation of voids, is that the internal diameter "d" of the passageway of the nozzle and/or discharge orifice of the respective described capsule embodiments be equal to or relatively close to the internal diameter "D" of the capsule body portion with no corners or shaped angles disposed in the transitional area thereinbetween. In this manner, the ultra dense composite material is caused to be displaced as a "slug" in being forced out of the discharge orifice during an extruding operation, with little or no resistance being imparted thereto as it begins sliding. Coating the internal surfaces of the described capsule constructions with a thin film of a lubricant compatible with the ultra dense composite material, functions to further reduce or minimize any sliding friction occurring between the "slug" of material and the internal walls of the capsule during extrusion. The use of a Teflon piston as described with respect to the embodiment of FIGS. 15–17 also aids in minimizing sliding friction.

It will be understood that the capsules described herein are preferably made of a suitable plastic material which is compatible with the composition of the ultra dense composite material dispensed thereby. Such plastic materials may be selected from the group consisting of polypropylene, nylon, delrin, and/or like materials such as previously taught in the dental capsule art herein cited.

The pistons may also be formed of similar type plastic materials and/or rubber or synthetic rubber or a fluoropolymer, e.g. Teflon, as described with respect to FIGS. 15 to 17.

While the described embodiments are particularly suitable for dispensing ultra-dense dental material by syringing from capsules having a discharge nozzle diameter "d" to body portion diameter "D" ratio of $$\frac{\text{``}d\text{''}}{\text{``}D\text{''}}$$

ranging from 0.60 to 1, the principle described herein may also permit the described constructions to be used with other dental material not as condensable or packable as the ultra high viscosity dental materials.

While the present invention has been described with respect to several embodiments, modifications and variations may be made without departing from the spirit or scope of this invention.

What is claimed is:

1. A dental capsule for dispensing a dental material directly to a prepared tooth by a syringing technique comprising:

a body portion defining a reservoir for containing a predetermined amount of dental material, said body portion having an internal diameter D, and said body portion having an opening at one end and a discharge nozzle at the other end, said discharge nozzle being angularly disposed relative to the axis of said body portion, a passageway extending through said discharge nozzle terminating at a discharge orifice, said passageway having an internal diameter whereby the ratio of said internal diameters $$\frac{\text{``}d\text{''}}{\text{``}D\text{''}}$$

range between 0.60 to 1, said discharge nozzle having a wall thickness which progressively decreases toward said discharge orifice, an elongated displaceable piston for sealing said opening, said piston having a diameter sized to be snugly received in said body portion and said passageway, said piston being sufficiently flexible so as to extend through said passageway angularly disposed relative to said body portion so as to extrude all of a dental material disposed in said passageway, wherein said walls of said discharge nozzle are sufficiently flexible to permit said piston to extend into said passageway.

2. A dental capsule as defined in claim 1 wherein said piston is cylindrical in shape and having similarly shaped opposed ends to render said piston bi-directional.

3. A dental capsule as defined in claim 2 wherein said piston has a substantially constant cross-sectional shape throughout the length thereof.

4. A dental capsule as defined in claim 3, wherein said piston is formed of a fluoropolymer type material.

5. A dental capsule as defined in claim 1 wherein said piston is cylindrical in shape and having similarly shaped end portions to render said piston bi-directional.

6. A dental capsule as defined in claim 5 wherein said end portions are blunt.

7. A dental capsule as defined in claim 1 and including a laterally outwardly extending flange circumscribing said body portion adjacent said opening at said one end of said body portion.

* * * * *